United States Patent
Masini

(10) Patent No.: US 7,815,644 B2
(45) Date of Patent: Oct. 19, 2010

(54) INSTRUMENTATION AND METHODS FOR REFINING IMAGE-GUIDED AND NAVIGATION-BASED SURGICAL PROCEDURES

(76) Inventor: Michael A. Masini, 2950 Hickory La., Ann Arbor, MI (US) 48104

( * ) Notice: Subject to any disclaimer, the term of this patent is extended or adjusted under 35 U.S.C. 154(b) by 1793 days.

(21) Appl. No.: 10/741,779

(22) Filed: Dec. 19, 2003

(65) Prior Publication Data

US 2005/0137599 A1    Jun. 23, 2005

(51) Int. Cl.
*A61F 2/44* (2006.01)
(52) U.S. Cl. .......................... 606/86 R; 606/87; 606/88; 606/79; 600/414
(58) Field of Classification Search .................. 606/79, 606/87, 88, 86 R, 82–85; 600/414; 623/20.14–20.36
See application file for complete search history.

(56) References Cited

U.S. PATENT DOCUMENTS

| | | | | |
|---|---|---|---|---|
| 2,554,763 | A * | 5/1951 | Wickman | 451/358 |
| 3,733,665 | A * | 5/1973 | Spriggs | 407/41 |
| 4,156,966 | A * | 6/1979 | Eubank | 30/166.3 |
| 4,467,801 | A * | 8/1984 | Whiteside | 606/88 |
| 4,952,213 | A * | 8/1990 | Bowman et al. | 606/79 |
| 5,263,498 | A * | 11/1993 | Caspari et al. | 128/898 |
| 5,364,402 | A * | 11/1994 | Mumme et al. | 606/88 |
| 5,423,822 | A * | 6/1995 | Hershberger et al. | 606/79 |
| 5,445,642 | A * | 8/1995 | McNulty et al. | 606/88 |
| 5,880,976 | A | 3/1999 | DiGioia III et al. | 364/578 |
| 5,995,738 | A | 11/1999 | DiGioia, III et al. | 395/500.32 |
| 6,002,859 | A | 12/1999 | DiGioia, III et al. | 395/500.32 |
| 6,205,411 | B1 | 3/2001 | DiGioia, III et al. | 703/11 |
| 6,287,312 | B1 * | 9/2001 | Clokie et al. | 606/85 |
| 6,361,563 | B2 * | 3/2002 | Terrill-Grisoni et al. | 623/20.11 |
| 6,514,259 | B2 | 2/2003 | Picard et al. | 606/88 |
| 6,723,102 | B2 | 4/2004 | Johnson et al. | |
| 6,725,080 | B2 | 4/2004 | Melkent et al. | |

(Continued)

OTHER PUBLICATIONS

BrainLab Brochure.
Stryker Navigation System Brochure.

*Primary Examiner*—Eduardo C Robert
*Assistant Examiner*—Jan Christopher Merene
(74) *Attorney, Agent, or Firm*—Gifford, Krass, Sprinkle, Anderson & Citkowski, P.C.

(57) ABSTRACT

Automated surgical procedures, including procedures carried out in conjunction with image-guided surgical navigation systems, are improved using tools and techniques to refine bone modifications. A system-level embodiment of the invention includes a memory for storing information relating to a desired modification of a bone, a bone-modification tool, and tracking apparatus for determining the position and orientation of the bone and the bone-modification tool to ensure that the modification performed by the tool corresponds to the desired modification. In the preferred embodiment, the bone-modification tool is used to refine a previously resected surface by a few millimeters or a few degrees to achieve the desired modification. A method of preparing a bone to receive a prosthetic implant according to the invention includes the steps of using an image-guided surgical navigation system to surface a bone, determining if the surface is optimized for the prosthetic implant, and if not, using a finishing tool in conjunction with the image-guided surgical navigation system to refine the surface. These steps may be repeated as desired to further optimize the surface.

15 Claims, 4 Drawing Sheets

U.S. PATENT DOCUMENTS

| | | | |
|---|---|---|---|
| 6,743,086 B2 * | 6/2004 | Nelson et al. | 451/527 |
| 6,892,090 B2 | 5/2005 | Verard et al. | |
| 6,917,827 B2 | 7/2005 | Kienzle, III | |
| 6,920,347 B2 | 7/2005 | Simon et al. | |
| 6,922,581 B2 | 7/2005 | Kienzle, III | |
| 6,925,339 B2 * | 8/2005 | Grimm et al. | 700/59 |
| 6,947,786 B2 | 9/2005 | Simon et al. | |
| 6,990,220 B2 | 1/2006 | Ellis et al. | |
| 7,008,430 B2 | 3/2006 | Dong et al. | |
| 7,130,676 B2 | 10/2006 | Barrick | |
| 7,174,202 B2 | 2/2007 | Bladen et al. | |
| 7,313,430 B2 | 12/2007 | Urquhart et al. | |
| 2001/0018589 A1 * | 8/2001 | Muller | 606/88 |
| 2002/0029045 A1 * | 3/2002 | Bonutti | 606/86 |
| 2002/0052606 A1 * | 5/2002 | Bonutti | 606/88 |
| 2002/0107522 A1 * | 8/2002 | Picard et al. | 606/88 |
| 2002/0133175 A1 * | 9/2002 | Carson | 606/130 |
| 2002/0138143 A1 * | 9/2002 | Grooms et al. | 623/17.11 |
| 2002/0193797 A1 * | 12/2002 | Johnson et al. | 606/79 |
| 2004/0087852 A1 | 5/2004 | Chen et al. | |
| 2004/0243134 A1 * | 12/2004 | Walker et al. | 606/79 |
| 2005/0065617 A1 * | 3/2005 | Moctezuma de la Barrera et al. | 623/908 |
| 2005/0154397 A1 | 7/2005 | Ashby et al. | |
| 2005/0203367 A1 | 9/2005 | Ahmed et al. | |
| 2006/0161052 A1 | 7/2006 | Colombet et al. | |
| 2006/0229624 A1 | 10/2006 | May et al. | |

* cited by examiner

INSTRUMENTATION AND METHODS FOR REFINING IMAGE-GUIDED AND NAVIGATION-BASED SURGICAL PROCEDURES

FIELD OF THE INVENTION

This invention relates generally to surgical procedures and, more particularly, to tools and techniques to refine bone modification and other steps encountered during automated surgical procedures.

BACKGROUND OF THE INVENTION

Computer-automated surgical procedures, variously known as image-guided or navigation-based techniques, are becoming increasing popular as a way of improving the accuracy and throughput of orthopaedic, neuro-surgical and other surgical cases. Companies now engaged in this market segment include Stryker, Medtronic Surgical Navigation Technologies (a unit of Medtronic), BrainLAB, Inc., Radionics, Inc. (a subsidiary of Tyco International), Surgical Navigation Network, Inc. (a division of Cedara Software), and Visualization Technology, Inc. Theses systems assist the surgeon in the placement of instruments, location and depth of bone cuts and placement of implant components during surgery.

By way of example, the Stryker Knee Navigation System includes a "smart camera" that provides two-way communication between the instruments, a video monitor, and minimally invasive wireless "pointers" and "trackers" incorporating infrared emitters. A knee-replacement procedure begins with the surgeon inserting two tracking pins, one into the distal femur and one into the proximal tibia. Then a tracking device, positioned to face the camera, is mounted on each of the pins. Using a pointer, the surgeon touches various locations of known anatomy to establish a reference system. The system collects this information, maps it and graphically shows it on the screen.

As the surgeon physically manipulates the joint, positional information appears on the computer monitor as two-dimensional graphics in real time. Coupled with images of key anatomical points and areas of bone deficiency and soft tissue, the surgeon is able to make very precise bone resections and then place the prosthesis with great accuracy. As the surgeon prepares to remove bone for placement of the knee implant, the Knee Navigation System also provides data regarding placement of the cutting jig, enabling the surgeon to make real time angular adjustments before the first cut. The system also provides postoperative data once the implant is in place.

One of the drawbacks of these and other systems involves the way in which resections are checked for accuracy. Currently, the surgeon uses a position-calibrated "paddle" having a flat surface that is placed against a particular cut. The visualization system then registers the position of the planar system and computes an estimate of accuracy. If the surgeon is "off," even by a few millimeters, the resection process must be re-entered and tested again. Apparatus and methods of streamlining this process would be welcomed.

SUMMARY OF THE INVENTION

This invention improves upon automated surgical procedures, including procedures carried out in conjunction with image-guided surgical navigation systems, by providing tools and techniques to refine bone modifications encountered during such procedures.

A system-level embodiment of the invention includes a memory for storing information relating to a desired modification of a bone, a bone-modification tool, and tracking apparatus for determining the position and orientation of the bone and the bone-modification tool to ensure that the modification performed by the tool corresponds to the desired modification.

In the preferred embodiment, the bone-modification tool is used to refine a previously resected surface by a few millimeters or a few degrees to achieve the desired modification. Alternatively the bone-modification tool may be used to perform an initial shaping, preferably in real time using a display for visualization.

Though different techniques may be used, the tracking apparatus includes position-indicating fixtures coupled to bone-modification tool(s) and the bone being modified. The bone-modification tool may assume the form of a milling machine, planer, sander or saw, and the modification may be used to prepare a surface to receive a prosthetic implant, whether joint-related or associated with an osteotomy or trauma fixation.

A method of preparing a bone to receive a prosthetic implant according to the invention includes the steps of using an image-guided surgical navigation system to prepare a surface to a bone, determining if the surface is optimized for the prosthetic implant, and if not, using a finishing tool in conjunction with the image-guided surgical navigation system to refine the surface. These steps may be repeated as desired to further optimize the surface.

In a preferred embodiment, the tool has a removable cutting portion so it may be exchanged as necessary to provide a sharp cutting surface. The cutting surface may be varied in the case of the "sander" for finer cuts when finishing a surface, or for rougher cuts, as indicated. The tool may cut by means of rotary motion, planar oscillations, or vibration. A planing attachment would, in particular, provide greater degrees of accuracy than a saw, the tip of which may be subject to deflection. The saw could thus be used for initial rough cuts, for example, with the sander or planar being used for corrections.

DETAILED DESCRIPTION OF THE INVENTION

Figure 1:
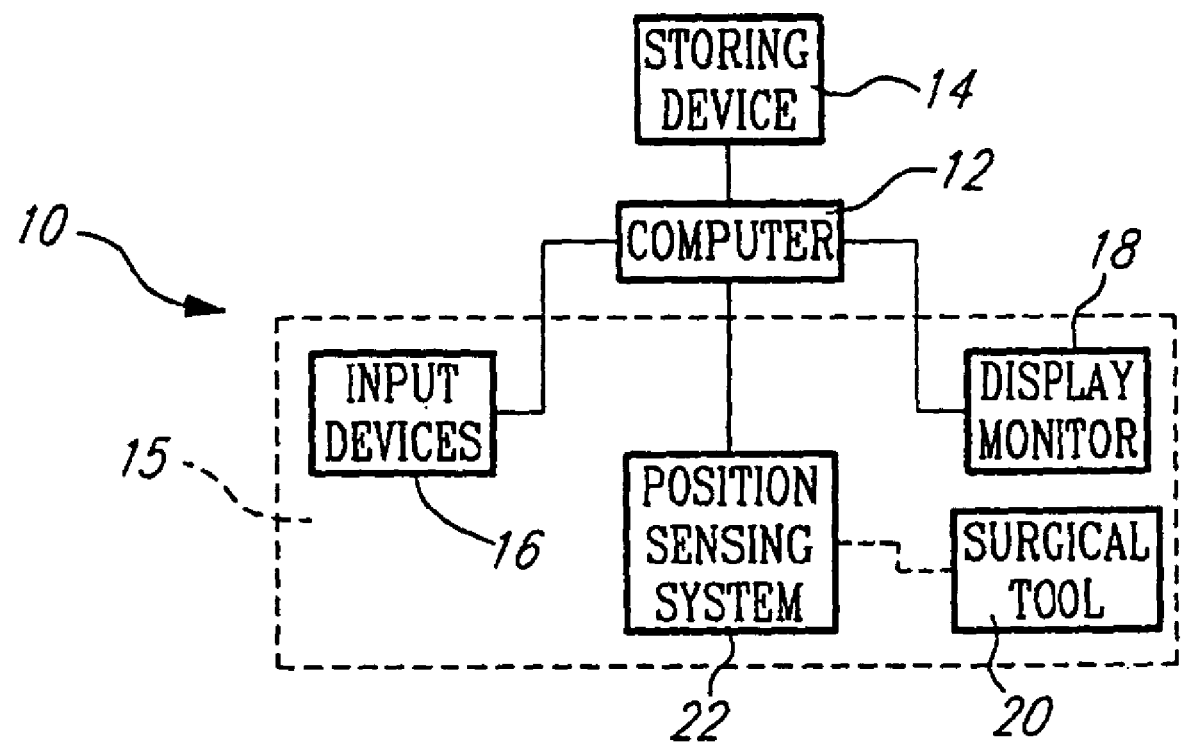
FIG. 1 SHOWS a typical image-guided surgical navigation system as disclosed in U.S. Pat. No. 6,533,737.

As a foundation for the detailed description of this invention, a typical image-guided surgical navigation system is provided in U.S. Pat. No. 6,533,737, the entire content of which is incorporated herein by reference. The system 10 in FIG. 1 includes a computer 12 having a memory (not shown), a storage device 14, and a user interface 15. The user interface 15 includes input devices 16, an output device in the form of a display monitor 18, a surgical tool 20, and a position sensing system 22.

The storage device 14 is used to store three-dimensional models of the surgical tool 20 and of the anatomical structures, in this case, in the form of a femur 24 and a tibia 26, (see FIG. 2) on which a surgical procedure is to be performed. The storage device 14 can be directly connected to the computer 12 via local wired or wireless connections, or remotely via a computer network, such as the Internet. The input devices 16 may include a keyboard and mouse, a touch screen or a voice-recognition system, or may be connected to a pointer. The output device 18 may be a video monitor or more advanced image-generation means such as three-dimensional display goggles. The surgical tool 20 can be, for example, an awl, a screwdriver to install, for example, an artificial ligament, or any tool used in surgical procedures.

Figure 2:
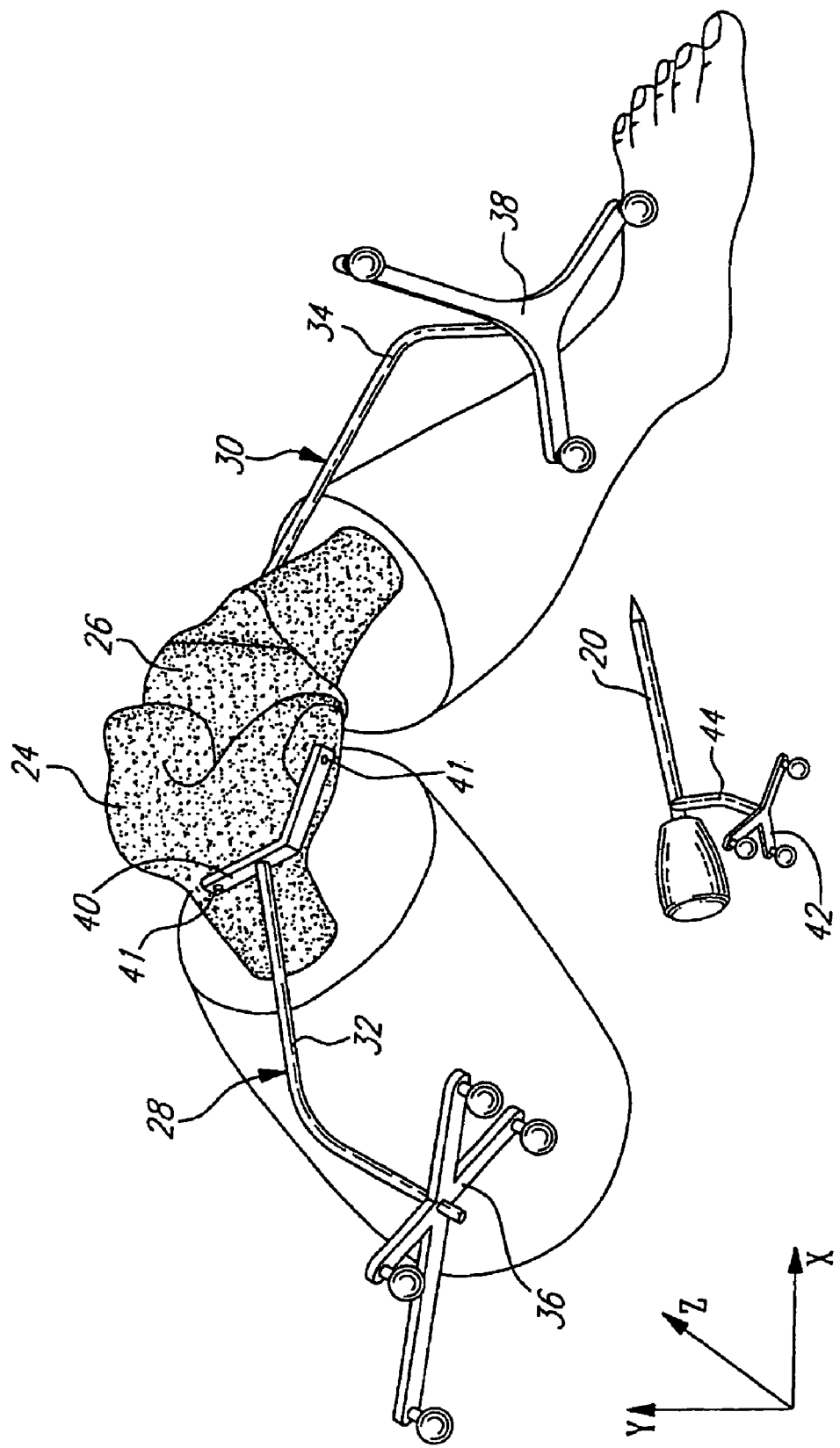
FIG. 2 shows a position sensing system including a position sensing device in the form of a video camera (not shown), connected to the computer via conventional connectors and reference clamps and secured respectively to the patient's femur and tibia.

Referring to FIG. 2, the position sensing system 22 includes a position sensing device, in the form of a video camera (not shown), connected to the computer 12 via conventional connectors and reference clamps 28 and 30, secured respectively to the patient's femur 24 and tibia 26. The reference clamps 28 and 30 in this case include bent rods 32, 34 and reference assemblies 36 and 38, secured to their respective rods 32 and 34. Reference assemblies 36 and 38 are of different shapes so that they can be discriminated by the computer 12. Each of reference clamps 28 and 30 also includes mounting brackets 40 (only one shown) to adequately secure the reference clamps to the tibia 24 and the femur 26, using small surgical screws 41 (only two shown). Similarly, a reference assembly 42 is secured by welding to the surgical tool 20 via a bent rod 44. The reference assembly 42 may, alternatively, include a mounting bracket to secure the reference assembly 42 on other surgical tools.

The operation of this particular prior art position sensing system will now be described. The camera is used to capture and to transfer to the computer 12 the image of the reference assemblies 36, 38 and 42 during the surgical procedure. A registration algorithm, including conventional registration method, is used to convert the real-time image in relative position between each of the reference assemblies 36, 38 and 42. Since the position, shapes and size of each reference assemblies 36, 38 and 42 are known to the computer 12, the relative position of the surgical tool 20 with respect to the anatomical structures 24 and 26 may be calculated.

The position sensing system 22 may also include a dedicated processor (not shown) that can determine the relative positions of the reference assemblies 36, 38 and 42 and/or the relative positions of the surgical tool 20 and anatomical structures 24 and 26 before sending that information to the computer 12. Other well known position sensing systems, such as, for example, a magnetic position sensing system, can also be used. In such a system, the camera is advantageously replaced by a magnetic field sensor and the reference assemblies are advantageously replaced by magnetic field emitters.

The first step of the method is to provide the computer 12 with three-dimensional models of the tibia 24, the femur 26 and the surgical tool 20. These models are transferred from the storage device 14 to the computer memory. The three-dimensional models may be obtained, for example, from two-dimensional slice images of the anatomical structures of interest, using three-dimensional reconstruction systems known to those of skill in the art. The slice images can be obtained, for example, by scanning the anatomical structures with a CT or a MRI scanner.

The second step is to calibrate the surgical tools 20 and the reference clamps 28 and 30. For example, this is accomplished by the computer 12, by performing transformations, first, from the reference assembly 42 to the tip of the surgical tool 20 and second, by selecting reference points on the three-dimensional models of the anatomical structures 24, 26 and by identifying the corresponding points on the anatomical structures 24 and 26. Of course, other calibration protocols could be used.

During the surgical procedure, the position sensing system 22 will first register the positions and orientations of the reference assemblies 36, 38 and 42 in the coordinate system of the position sensing system (represented by the axes X,Y and Z in FIG. 2). Then the orientations and positions of the surgical tool 20, the tibia 24 and the femur 26 are transformed into virtual orientations and position in the reference system of the three-dimensional models. The three-dimensional models of the tool 20 and of the anatomical structures are then reproduced on the display monitor 18 in their new orientations and at their new positions in the computer reference system.

The registration process by the position sensing system 22 and the regeneration of the image on the display monitor 18 are performed at a rate sufficient to allow real-time display and interaction with the three-dimensional models. The display is said to be in real-time, since movement of the models is perceived as being continuous, without flicker effect, and synchronized with the movements of the anatomical structures 24, 26 and of the surgical tool 20.

The computer 12 is also programmed to allow visualization of the anatomical structures and of the surgical tool as it would be seen from different points of view selected using the input devices 16. The computer 12 is may further be programmed to display the anatomical structures as translucent (partially transparent) objects, allowing the surgeon to better visualize the interaction between the surgical tool 20 and the anatomical structures.

U.S. Pat. No. 6,533,737 goes on to describe the replacement of the anterior cruciate ligament (ACL) of the knee with an artificial ligament using the disclosed system and method. Following the appropriate calibration procedure, the surgeon uses the surgical tool 20, in the form of an awl, to identify on the patient's tibia 24 and femur 26 the two points 46 and 48 where he believes he should place the artificial ligament. From those two points, a virtual model of the ligament is created by the computer 12 and displayed on the monitor 18 using stored models of the tibia. The surgeon then flexes the patient's knee in order to obtain a set of position measurements. As it has been described hereinabove, the positions of the tibia 24 and of the femur 26 will be determined by the computer 12 and modeled on the monitor 18.

According to these positions, the computer 12 will calculate the distance between the two specified points at different flexion angles. A message is then displayed on the monitor 18, informing the surgeon whether or not the isometry constraint is respected. If the constraint is not within a pre-specified tolerance, the surgeon may change the proposed artificial ligament position and perform another leg flexion to verify isometry. Once a position is found satisfying, the surgeon can use the system 10 to perform the surgical procedure. More specifically, the surgeon can visualize the positions of the two points 46 and 48 on the three-dimensional computer models displayed on the monitor to guide him while drilling the holes that will be used to fix the artificial ligament 50.

Figure 3:
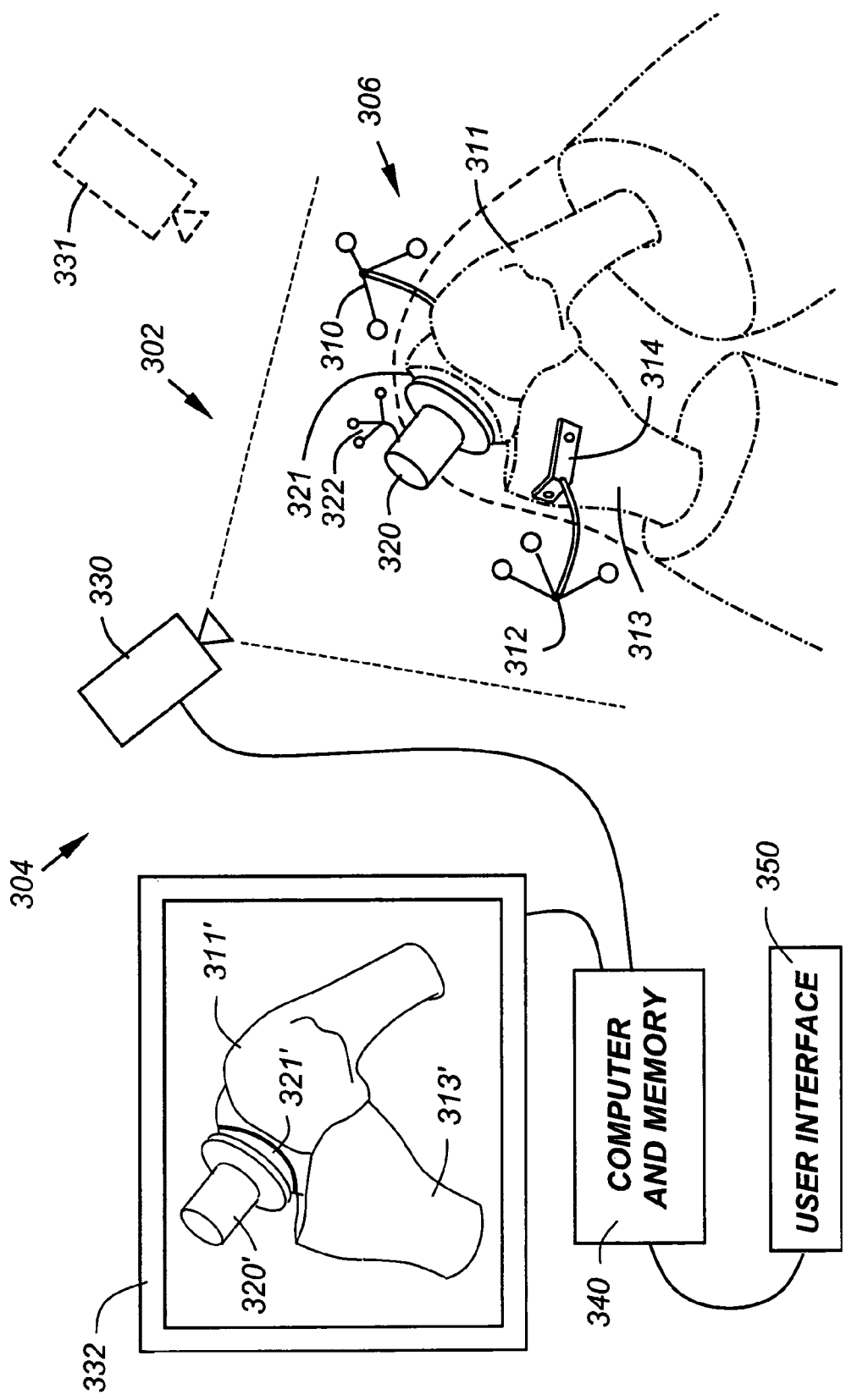
FIG. 3 illustrates a preferred embodiment of the invention in conjunction with knee replacement procedure.

With this background information, the reader's attention is now directed to FIG. 3, which illustrates a preferred embodiment of the invention generally at 300, in conjunction with knee replacement procedure shown generally at 306. The system includes one or more fixtures such as 310 and 312, mountable to bones such as distal femur 311 and proximal tibia 313 through plates 314 providing a temporary yet rigid connection. The fixtures 310, 312 each include a plurality of devices operative to determine the position and orientation of the bones to which they are attached in multiple dimensions. These devices may be passive, in the sense that they have a particular size, shape or color allowing a visual sensing system such as camera 330 to locate the devices in space, or they may be "active," in the sense that they may include optical, acoustic and/or electromagnetic transmitters to assist in position/orientation location. It will be appreciated by those of skill that the item 330 may either be a video camera operating in the visible or infrared region of the spectrum, or may be some other type of unit operative to sense. The position and orientation of the device is affixed to fixtures 310, 312. It would further be appreciated that additional sensors such as 331 may be provided for a more complete coverage throughout the surgical field. Furthermore, although this example is based upon knee replacement, the sensors may be adapted for placement on other bones, different types of orthopedic procedures such as total hip replacement, shoulder replacement, other bones within the extremities, and other procedures including osteotomies and trauma fixation.

As discussed above, a video camera or other type of sensor 330 includes a field of view which finds and recognizes the devices on fixtures 310, 312, so that the position and orientation of the bones 311, 313 may be determined in multiple dimensions. Preferably, the fixtures 310, 312 each contain three or more devices, enabling the bones to be identified in three-space.

The camera or sensor 330 is interfaced through a computer with storage capabilities 340, which, in turn, communicates with a display 332 and user interface 350. The display 332 is operative to generate a model of the bone or bones being operated on, as 311', 313', which may be obtained through any of the techniques discussed hereinabove, including the use of 2-D anatomical slices, 3-dimensional reconstruction systems, CT, MRI scanners, fluoroscopy, or synthesis by anatomic locating sensors.

Unique to this invention, a tool 320 is provided, having its own fixture 322 with sufficient devices to determine the position and orientation of the tool 320 in multiple dimensions, preferably three dimensions. In contrast to existing systems, the tool 320 is not just a pointer or resection-sensing "paddle," but rather, is itself a bone-modification tool. In a preferred embodiment, the tool 320 takes the form of a sander or milling machine, operative to refine a previously made resection 321, so as to bring that plane into conformance with a desired surface. Given that the physical relationship between the plane of the tool 320 and the devices on fixture 322 are known, the system may, in real time, track the modification of the bone 311, displaying the results on the screen 332. Preferably, the system not only shows the surface as it is modified, but also displays a desired goal such as 321' on the screen, enabling the surgeon to see the progress in approaching the desired degree of modification.

Figure 4:
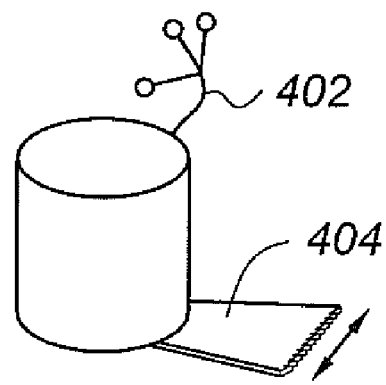
FIG. 4 shows an oscillating saw.

The invention is not limited to refinements to previously made resections or modifications, but may, itself, be used for primary bone modification, including initial resections or other shaping procedures. In such a case, a tool of the type shown in FIG. 4 may be provided, in this case an oscillating saw. Again, since the physical relationship between the elements on fixture 402 are known, the plane of the blade 404 may be determined in multiple dimensions and shown on display screen 332 as a particular procedure is performed.

Figure 5:
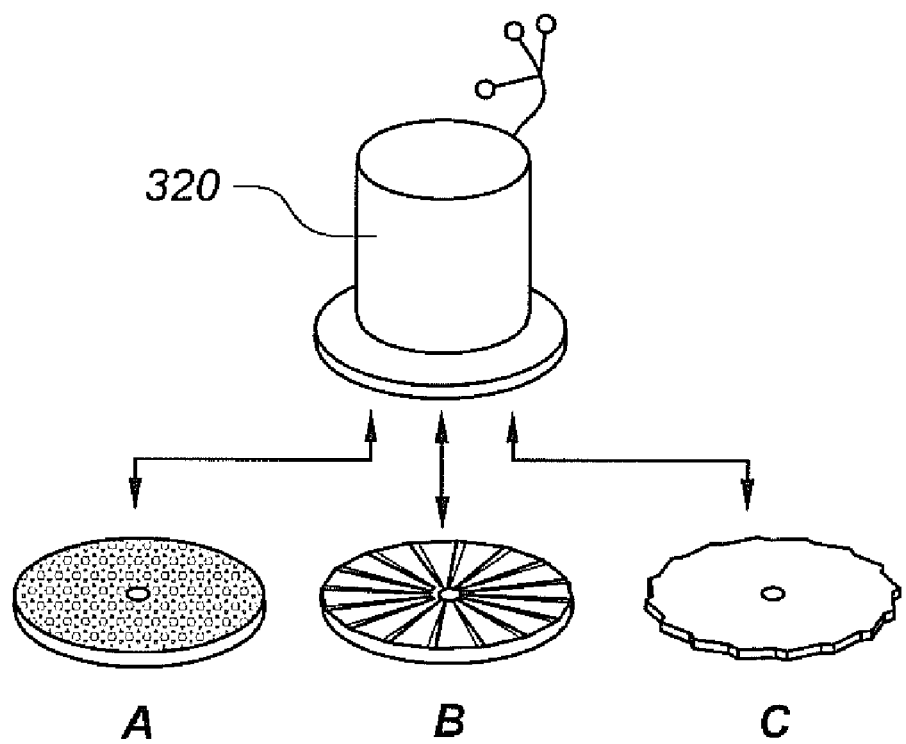
FIG. 5 shows sander, planer/milling and rotating saw attachments.

In a preferred embodiment, the tool has a removable cutting portion so it may be exchanged as necessary to provide a sharp cutting surface (FIG. 5). The cutting surface may be varied in the case of the "sander" "A" for finer cuts when finishing a surface, or for rougher cuts, as indicated. The tool may cut by means of rotary motion, planar oscillations, or vibration. A planing or milling attachment "B" would, in particular, provide greater degrees of accuracy than a saw, the tip of which may be subject to deflection. The saw "C" could thus be used for initial rough cuts, for example, with the sander or planar being used for corrections.

I claim:

1. A method of refining a bone surface to receive a prosthetic implant, comprising the steps of:
   a) using an image-guided surgical navigation system to create an initial rough cut on a bone,
   b) using a finishing tool to which there is mounted a fixture with devices to determine the position and orientation of the tool in multiple dimensions to compare the initial rough cut to an optimal surface to determine if the initial rough cut is optimized for the prosthetic implant; and
   c) using the finishing tool in conjunction with the image guided surgical navigation system to refine the initial rough cut by a few millimeters or a few degrees to establish a refined surface that is optimized for the prosthetic implant.

2. The method claim 1, including the steps of repeating step c) as desired to further refine the surface.

3. The method claim 1, wherein the finishing tool includes the provision of a milling machine.

4. Tile method claim 1, wherein the finishing tool includes the provision of a planer.

5. The method claim 1, wherein the finishing tool includes the provision of a sander.

6. The method claim 1, wherein the finishing tool includes the provision of a resecting tool.

7. The method claim 1, wherein the optimal surface is determined by 2-D anatomical slices, 3-dimensional reconstruction systems, CT, MRI scanners, fluoroscopy, or synthesis by anatomic locating sensors.

8. The method claim 1, wherein the prosthetic implant is joint-related.

9. The method of claim 3, including the step of providing a milling machine with a removable milling implement that may be replaced.

10. The method of claim 4, including the step of providing a planar with a removable planning implement that may be replaced.

11. The method of claim 5, including the step of providing a sander with a removable sanding surface that may be replaced.

12. The method of claim 5, including the step of providing a resecting tool with a removable blade that may be replaced.

13. The method of claim 1, wherein the refinement of the bone using the finishing tool is monitored by the tracking apparatus in real time.

14. The method of claim 1, including the step of providing visual representation of the finishing tool and the surface being refined.

15. The method of claim 1, including the step of providing a visual representation of the finishing tool and the surface being refined, the visual representation further including a desired goal enabling a user to visualize progress associated with approaching a desired degree of modification.

* * * * *